United States Patent [19]

Tarbet et al.

[11] Patent Number: 5,078,978
[45] Date of Patent: Jan. 7, 1992

[54] PYRIDINE-CONTAINING ALKOXYSILANES BONDED TO INORGANIC SUPPORTS AND PROCESSES OF USING THE SAME FOR REMOVING AND CONCENTRATING DESIRED IONS FROM SOLUTIONS

[75] Inventors: Bryon J. Tarbet; Jerald S. Bradshaw; Krzysztof E. Krakowiak; Reed M. Izatt; Ronald L. Bruening, all of Provo, Utah

[73] Assignee: Brigham Young University, Provo, Utah

[21] Appl. No.: 432,199

[22] Filed: Nov. 6, 1989

[51] Int. Cl.$^5$ .......................... C01G 55/00; G07F 7/18
[52] U.S. Cl. .......................... 423/22; 75/313; 75/713; 75/722; 210/688; 210/912; 210/913; 210/914; 423/24; 423/46; 423/54; 423/63; 423/100; 423/139; 546/14
[58] Field of Search .......... 75/312, 722; 210/912, 210/913, 914, 688; 423/24, 49, 54, 63, 100, 139, 22

[56] References Cited

U.S. PATENT DOCUMENTS

| | | | |
|---|---|---|---|
| 3,957,504 | 5/1976 | Ho et al. | 423/24 |
| 4,051,230 | 9/1977 | Miyauchi | 423/24 |
| 4,448,694 | 5/1984 | Plueddemann | 210/688 |
| 4,942,023 | 7/1990 | De Schepper et al. | 423/24 |
| 4,952,321 | 8/1990 | Bradshaw et al. | 210/688 |
| 4,959,153 | 9/1990 | Bradshaw et al. | 210/688 |

Primary Examiner—Robert T. Bond
Attorney, Agent, or Firm—Terry M. Crellin

[57] ABSTRACT

A method is disclosed for the quantitative removal and concentration of desired transition metal ions from a source solution which may contain larger concentrations of other metal and H$^+$ ions. The method comprises bringing the source solution into contact with a compound comprising a pyridine containing ligand covalently bonded through an organic spacer silicon grouping to a solid inorganic support. The pyridine portion(s) of the compound has an affinity for the desired metal ions to form a complex thereby removing the desired metal ions from the source solution. The desired metal ions are removed from the compound by contacting the compound with a much smaller volume of a receiving solution having a greater affinity for the desired metal ions than does the pyridine ligand portion of the compound. The concentrated metal ions thus removed may be recovered by known methods. The process is useful in removing unwanted metal ions from water streams and in the treatment of waste streams such as those containing metal ions from emulsions found in the treatment of photographic and x-ray films. The invention is also drawn to novel intermediates comprising pyridine containing ligands covalently bonded through a spacer grouping to a silane and to the final compounds formed by reacting the intermediates with a hydrophilic inorganic solid support material.

13 Claims, No Drawings

PYRIDINE-CONTAINING ALKOXYSILANES BONDED TO INORGANIC SUPPORTS AND PROCESSES OF USING THE SAME FOR REMOVING AND CONCENTRATING DESIRED IONS FROM SOLUTIONS

FIELD OF THE INVENTION

This invention relates to intermediate pyridine containing hydrocarbons covalently bonded to alkoxysilanes, the covalent bonding of such intermediates to inorganic solid supports and to a process for removing and concentrating certain desired ions, from solutions wherein such ions may be admixed with other ions which may be present in much higher concentrations by the use of such pyridine-alkoxysilane-solid supported materials. More particularly, this invention relates to a process for removing such ions from an admixture with others in solution by forming a complex of the desired ions with compounds composed of a pyridine-alkoxysilane moiety covalently bonded to an inorganic matrix by flowing such solutions through a column packed with such pyridine-alkoxysilane-solid supported compounds and then breaking the complex of the desired ion from the compounds to which such ion has become attached by flowing a receiving liquid in much smaller volume than the volume of solution passed through the column to remove and concentrate the desired ions in solution in the receiving liquid. The concentrated ions thus removed may then be recovered by known methods.

BACKGROUND OF THE INVENTION

Effective methods for the recovery and/or separation of particular ions such as certain transition metal ions, of which $MN^{2+}$, $Ni^{2+}$, $Cu^{2+}$ and $Cd^{2+}$ are illustrative, from other ions such as $H^+$, $Na^+$, $K^+$, $Mg^{2+}$, $Ca^{2+}$, and $Fe^{3+}$, and, the recovery and/or separation of metal ions, such as the transition metal ions, from other metal ions in water supplies, waste solutions, e.g., from emulsions on photographic and X-ray film, particularly those which contain large amounts of $H^+$, represent a real need in modern technology. These ions are often present at low concentrations in solutions containing other ions at much greater concentrations. Hence, there is a real need for a process to selectively concentrate and recover these ions.

It is known that pyridine containing hydrocarbon ligands present as solutes in a solvent such as water, are characterized by their ability to selectivity form strong bonds with many transition metal cations such as $Mn^{2+}$, $Ni^{2+}$, $Cu^{2+}$, $Cd^{2+}$, and others or groups of these ions present as solutes in the same solvent, even in the presence of relatively large amounts of $H^+$, and other common cations such as $Na^+$, $K^+$, $Mg^{2+}$, $Ca^{2+}$, and $Fe^{3+}$, as described by Smith et al., *CRITICAL STABILITY CONSTANTS*, Volumes 2, 5, 6, Plenum Press, New York, 1975, 1982, 1989. However, researchers have not previously been able to incorporate pyridine-containing hydrocarbon ligands into separation systems where the behavior of the pyridine-containing ligands in the separation systems, in comparison to that of the pyridine-containing ligand as a solute, is unchanged and the pyridine-containing ligand will remain in the separation system covalently bonded to an inorganic solid support such as silica gel. Articles such as those entitled *SILANE COMPOUNDS FOR SILYLATING SURFACES* by E. P. Plueddemann, in "Silanes, Surfaces and Interfaces Symposium, Snowmass, 1985," Ed. by D. E. Leyden, Gordon and Breach, Publishers, 1986, pp. 1-25 and *SILANE COUPLING AGENTS* by E. P. Plueddemann, Plenum Press, 1982, pp. 1-235 list many different types of organic materials which have been attached to silane compounds and discusses some of their properties. The preparation and uses of pyridine-containing hydrocarbons attached to silane or silica have not been disclosed in the above mentioned articles or in any existing patents. Representative of patents describing the attachment of pyridine-containing hydrocarbons to hydrophobic polymers are Hancock et al., UK Patent 2,071,120, issued Sept. 16 1981; Jones et al., U.S. Pat. No. 3,998,924, issued Dec. 21, 1976; Grinstead, U.S. Pat. No. 4,451,375, issued May 29, 1984; Grinstead et al., U.S. Pat. 4,031,038, issued June 21, 1977; and Belgian Patent 887,872, published July 1, 1981. However, the materials described in these patents have ion exchange properties which alter selectivity as well as reduced and altered pyridine complexing properties due to the hydrophobic support. Thus, the unique complexing properties of certain pyridine containing hydrocarbons and the ability to attach these pyridine-containing complexing agents to inorganic solid supports such as sand or silica gel without reducing their ability to complex certain metal ions has heretofore been unknown but has been found to be of utmost importance in the industrial use of the pyridine-containing hydrocarbon ligands. That is the subject matter of the present invention.

SUMMARY OF THE INVENTION

The intermediate compounds of the present invention comprise suitable pyridine containing ligands which are covalently bonded through a spacer grouping to a silicon atom and are represented by the following Formula 1:

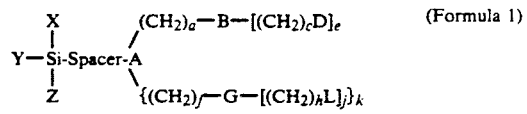
(Formula 1)

wherein Spacer is a grouping having from 1 to 10 carbon atoms and which is of a functional nature that it is sufficiently hydrophilic to function in an aqueous environment and will separate the pyridine ligand from the solid support surface to maximize the interaction between the ligand and desired ion being separated and is preferably a member selected from the group consisting of lower alkyl, aryl, glycidyl and alkylamino. A is a member selected from the group consisting of N, NH, S and O. B, D, G, and L are each members selected from the group consisting of $NR_x$, 2-pyridyl or 2-substituted pyridyl with x being an integer of 1 or 2 depending upon whether $NR_x$ is in intermediate part of a chain with x being 1 or forms an end grouping with x being 2. The letters a, c, g and h represent integers ranging from 1 to 5; e and j are each integers ranging from 0 to 5; and k is an integer of 0 or 1 with the proviso that k must be 0 when A is NH, S or O and k must be 1 when A is N. R is a member selected from the group consisting of H, lower alkyl, substituted lower alkyl, pyridyl or substituted pyridyl. By substituted alkyl or substituted pyridyl is meant alkyl or pyridyl groups containing substituents such as halogen, amino, alkyl amino and the like which do not interfere with the ability of the compound to function according to the invention. At least one of B or D and at least one of G or L must be a 2-pyridyl or substituted 2-pyridyl group. By pyridyl or pyridine is meant a six membered heterocyclic ring containing one nitrogen atom. However, fused ring structures such as, quinolines, pyridopyridines, phenanthrolines (diazaphenanthrenes) such as 1,10-phenanthroline (4,5-diazaphenanthrene) and joined ring structures such as bipyridines, terpyridines, etc. are within the scope of this definition as pyridine analogs. X, Y and Z are each a member selected from the group consisting of Cl, Br, I, alkyl, alkoxy, substituted alkyl or substituted alkoxy. X, Y and Z are functionally classified as leaving groups, i.e. groups attached to the silicon atom which, when reacted with an O-solid hydrophilic support material, may leave or be replaced by the O-solid support.

The above pyridine and silicon containing intermediates are covalently bonded to an inorganic matrix to produce a compound of Formula 2:

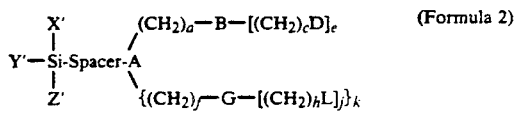
(Formula 2)

wherein all symbols have the meanings given above except X', Y' and Z' which are each members selected from the group consisting of Cl, Br, I, alkyl, alkoxy, substituted alkyl or substituted alkoxy and O-solid support with the proviso that at least one of X', Y' and Z' must be O-solid support. When X', Y' and Z' are other than O-solid support they are functionally classified as leaving groups, as above defined, which have not been reacted with the O-solid hydrophilic support material. Hence, they are functional groups left over after reacting a silicon containing spacer group with the solid hydrophilic support and have no direct function in the interaction between the cation-ligand-matrix and the desired ion and the pyridine ligand-attached to the solid support. Solid support is a member selected from the group consisting of silica, zirconia, titania, alumina, nickel oxide or other hydrophilic inorganic supports and mixtures thereof. Alkyl or alkoxy means a 1-6 carbon member alkyl or alkoxy group which may be substituted or unsubstituted, straight or branched chain. By substituted is meant substituted by groups such as Cl, Br, I, NO$_2$ and the like.

Typical silicon containing spacer groups for reacting with a pyridine ligand material to form the intermediate compounds of Formula 1 are as follows: dimethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid p-(chloromethyl)phenyltrimethoxysilane; vinyltriethoxysilane; 3-bromopropyltriethoxysilane; 3-glycidoxypropyltrimethoxysilane and the like.

The pyridine ligand covalently bonded to solid supports as shown in Formula 2 are characterized by high selectivity for and removal of desired metal ions or groups of desired metal ions, such as transition metal ions, present at low concentrations from source solutions containing a mixture of these desired metal ions with the ions one does not desire to remove which may be present in much greater concentrations in the source solution including hydrogen ions. The separation is effected in a separation device such as a column through which the source solution is flowed. The process of selectively removing and concentrating the desired metal ions is characterized by the ability to selectively and quantitatively complex the desired metal ions to the pyridine ligand portion of the pyridine containing solid support system, from a large volume of solution, even though the desired metal ions may be present at low concentrations. The desired ions thus separated are subsequently recovered from the separation column by flowing through it a small volume of a receiving phase which contains a solubilized reagent which need not be selective, but which will quantitatively strip the desired ions from the pyridine ligand containing solid support matrix. The recovery of the desired metal ions from the receiving phase is easily accomplished by known procedures.

The invention also includes a process for covalently binding the pyridine ligand moiety to a silicon containing spacer moiety to form the intermediate compounds of Formula 1. Additionally, the invention includes a process for further reacting the compounds of Formula 1 with an inorganic solid support to form the compounds of Formula 2.

DETAILED DESCRIPTION OF THE INVENTION

As summarized above, present invention is drawn to novel pyridine-containing hydrocarbon ligands covalently bound through a spacer to a silicon moiety to form novel intermediate compounds of Formula 1. The invention further is drawn to the covalent bonding of these novel intermediates to solid support materials to form the compounds of Formula 2. The invention is also drawn to the concentration and removal of certain desired metal ions, such as transition metal ions, from other metal ions in water supplies and waste solutions such as from emulsions on photographic and x-ray films. The process of the invention is particularly adaptable to recovery of metal ions from solutions containing large amounts of hydrogen ions. Such solutions from which such ions are to be concentrated and/or recovered are referred to herein as "source solutions". In many instances the concentration of desired ions in the source solutions will be much less than the concentration of other metal ions from which they are to be separated.

The concentration of desired ions is accomplished by forming a complex of the desired ions with a pyridine ligand solid support compound shown in Formula 2 and flowing a source solution containing the desired ions through a column packed with a pyridine ligand-solid support compound to attract and bind the desired metal ions to the pyridine ligand portion of such compound and subsequently breaking desired cation bound-pyridine ligand compound-complex by flowing a receiving liquid in much smaller volume than the volume of source solution passed through the column to remove and concentrate the desired ions in the receiving liquid solution. The receiving liquid or recovery solution forms a stronger complex with the desired transition metal ions than does the pryidine ligand and thus the desired metal ions are quantitatively stripped from the pyridine ligand containing solid support compound in concentrated form in the receiving solution. The recovery of desired metal ions from the receiving liquid are accomplished by known methods.

The intermediate pyridine-containing ligands bound to a silicon through a spacer grouping as represented by Formula 1 may be prepared by reacting a silane-spacer compound with a pyridine ligand compound as follows:

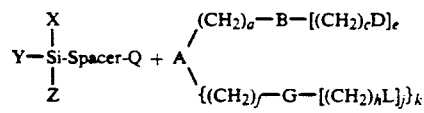

wherein Q and A are reactive groups such as epoxy and amino respectively which will react with each other allowing the formation of the compound of Formula 1 and wherein all other symbols have the meanings given above. When Q is epoxy, the epoxy group reacts with A in such a manner that Q becomes part of the spacer to form a linkage —CH(OH)CH$_2$—A=.

EXAMPLE 1

A pryidine containing ligand was prepared by mixing pyridine-2-carboxaldehyde (0.5 g, 5 mmol) with 2-(aminomethyl)pyridine at 0° C. The mixture was stirred for onehalf hour. Then a mixture of sodium borohydride and methanol (1 eq) was added and the mixture was refluxed for 24 hours. The complex was decomposed with dilute HCl, the solvents were removed and the product was extracted using sodium carbonate-water and chloroform. The chloroform was evaporated and the resulting product was reacted with 3-glycidoxypropyltrimethoxysilane (1 eq) in toluene at 50° C. for 24 hours, thereby producing a ligand of the formula:

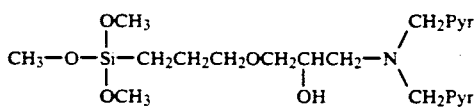

which corresponds to Formula 1 wherein X, Y and Z are each methoxy; Spacer is glycidoxypropyl; A is N; a, f and k are each 1; B and G are each 2-pyridyl; and e and j are 0.

EXAMPLE 2

In this example the process was repeated except the starting materials we re 2,6-pyridinedicarboxaldehyde and 2-(aminomethyl)pyridine in a 1:2 molar ratio. The reduced product was again allowed to react with 3-glycidoxypropyltrimethoxysilane in toluene to produce a compound of the formula:

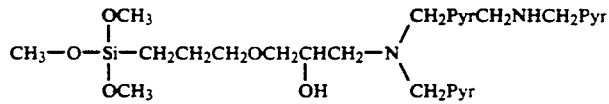

which corresponds to Formula 1 wherein X, Y and Z are each methoxy; Spacer is glycidoxypropyl; A is N; a, c, f and k are each 1; e is 2; B is 2,6-pyridyl, D is NH (first occurance) and 2-pyridyl (second occurrance); G is 2-pyridyl; and j is 0.

EXAMPLE 3

In this example the process was repeated except the starting materials were pyridine-2-carboxaldehyde and triethylenetetramine in a 2:1 molar ratio at 0° C. After reduction as above, the product is reacted with 3-glycidoxypropyltrimethoxysilane in toluene to produce a compound of the formula:

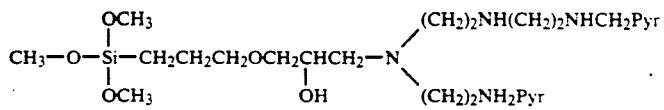

which corresponds to Formula 1 wherein X, Y and Z are each methoxy; Spacer is glycidoxypropyl; A is N; e is 2; h, j and k are each 1; B and G are each NH; a, f are each 2; c is 2 (first occurrence) and 1 (second occurrence); D is NH (first occurrence) and 2-pyridyl (second occurrence); and L is 2-pyridyl.

The compounds prepared in Examples 1-3 above can be further reacted with a solid support material to provide compounds of Formula 2 by replacing one or more of X, Y and Z with an O-solid support. This is accomplished by placing a compound represented by Formula 1 dissolved in a suitable solvent such as toluene in a suitable vessel and adding an appropriate amount of O-solid support material. This mixture is stirred and heated at a temperature of up to 100 degrees C. for a time sufficient to allow covalent bonding between the O-solid support and the silicon atom to take place. Usually from about one to 24 hours is sufficient. As previously stated suitable O-solid support materials include silica, zirconia, titania, alumina, nickel oxide or other hydrophilic inorganic supports and mixtures thereof.

EXAMPLE 4

To a flask outfitted with a mechanical stirrer and containing 1.75 grams of the pyridine-ligand silane of Example 1 contained in 25 mls of toluene was added 10 grams of silica gel. The flask was heated to a temperature of between about 55° and 95° C. and stirred overnight. The final product was collected by filtration and dried. This product corresponds to Formula 2 wherein X', Y' and Z' are either methoxy or O-silica with at least one, and on the average two, of the three being O-silica. Hence, on the average, X' and Y' are O-silica; Z is methoxy; Spacer is glycidoxypropyl; A is N; a, f and k are each 1; B and G are each 2-pyridyl; and e and j are 0. The product may therefore be represented by the formula:

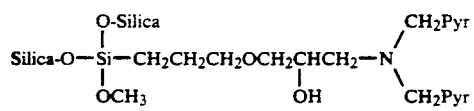

EXAMPLE 5

To a flask outfitted with a mechanical stirrer and containing 2.25 grams of the pyridine-ligand silane of Example 2 contained in 25 mls of toluene was added 10 grams of silica gel. The flask was heated to a temperature of between about 55° and 95° C. and stirred overnight. The final product was collected by filtration and dried. This product corresponds to Formula 2 wherein X', Y' and Z' are either methoxy or O-silica with at least one, and on the average two, of the three being O-silica. Hence, on the average, X' and Y' are O-silica; Z is methoxy; Spacer is glycidoxypropyl; A is N; a, c, f and k are each 1; e is 2; B is 2,6-pyridyl; D is NH (first occurrence) and 2-pyridyl (second occurrence); G is 2-pyridyl; and j is 0. The product may therefore be represented by the formula:

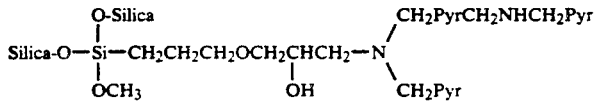

EXAMPLE 6

To a flask outfitted with a mechanical stirrer and containing 1.25 grams of the pyridine-ligand silane of Example 3 contained in 25 mls of toluene was added 10 grams of silica gel. The flask was heated to a temperature of between about 55° and 95° C. and stirred overnight. The final product was collected by filtration and dried. This product corresponds to Formula 2 wherein X', Y' and Z' are either methoxy or O-silica with at least one, and on the average two, of the three being O-silica. Hence, on the average, X' and Y' are O-silica; Z is methoxy; Spacer is glycidoxypropyl; A is N; e is 2; h, j and k are each 1; B and G are each NH; a, f, are each 2; c is 2 (first occurrence) and 1 (second occurrence); D is NH (first occurrence and 2-pyridyl (second occurrence); and L is 2-pyridyl. The product may therefore be represented by the formula:

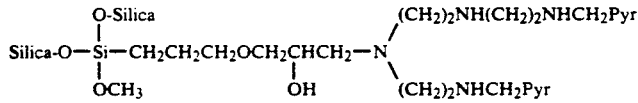

The process of selectivity and quantitatively concentrating and removing a desired ion or group of desired ions present at low concentrations from a plurality of other undesired ions in a multiple ion source solution in which the undesired ions may be present at much higher concentrations comprises bringing the multiple ion containing source solution into contact with a pyridine-ligand solid support compound shown in Formula 2 which causes the desired metal ion(s) to complex with the pyridine ligand portion of the compound and subsequently breaking or stripping the desired ion from the complex with a receiving solution which forms a stronger complex with the desired ions than does the pyridine ligand. The receiving or recovery solution contains only the desired metal ions in a concentrated form. Preferably the pyridine-ligand solid support compound will be contained in a column wherein the source and receiving solutions can flow through by gravity. If desired, the flow rate of these solutions can be increased by applying pressure (with a pump) on the top of the column or applying a vacuum in the receiving vessel.

The pyridine-ligand solid support functions to attract the desired metal cations according to Formula 3:

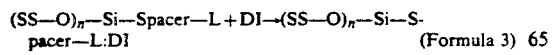

Except for DI, Formula 3 is an abbreviated form of Formula 2 wherein SS stands for solid support, n is an integer of 1-3 and L stands for a pyridine containing ligand. DI stands for desired ion being removed.

Once the desired metal ions are bound to the pyridine containing ligand, they are subsequently separated by use of a smaller volume of a receiving liquid according to Formula 4:

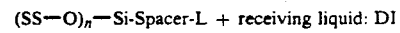

The preferred embodiment disclosed herein involves carrying out the process by bringing a large volume of the source multiple ion solution into contact with a pyridine ligand-solid support compound of Formula 2 in a separation column through which the mixture is first flowed to complex the desired metal ions (DI) with the pyridine ligand-solid support compound as indicated by Formula 3 above, followed by the flow through the column of a smaller volume of a receiving liquid, such as aqueous solutions of $Na_2S_2O_3$, $NH_3$, $NaI$, EDTA and others which form a stronger complex with the desired metal ion than does the pyridine containing ligand bound to the solid support. In this manner the desired metal ions are carried out of the column in a concentrated form in the receiving solution. The degree or amount of concentration will obviously depend upon the concentration of desired metal ions in the source solution and the volume of source solution to be treated. The specific receiving liquid being utilized will also be a factor. Generally speaking the concentration of desired transition metal ions in the receiving liquid will be from 20 to 1,000,000 times greater than in the source solution. Other equivalent apparatus may be used instead of a column, e.g., a slurry which is filtered, washed with a receiving liquid to break the complex and recover the desire metal ion(s). The concentrated desired metal ions are then recovered from the receiving phase by known procedures.

Illustrative of desired transition metal ions which have strong affinities for pyridine containing ligands bound to solid supports are $Cu^{2+}$, $Ni^{2+}$, $Zn^{2+}$, $Mn^{2+}$, $Co^{2+}$, $Cd^{2+}$, $Hg^{2+}$, $Pd^{2+}$, $Rh^{3+}$, $Co^{3+}$, $Fe^{2+}$, $Ir^{3+}$, $Pt^{2+}$, $Pt^{4+}$ and $Ru^{3+}$. This listing of preferred cations is not comprehensive and is intended only to show the types of preferred metal ions which may be bound to pyridine containing ligands attached to solid supports in the manner described above.

Removal of Desired Molecules With Cation-Ligand-Matrix Compounds

The following Examples demonstrate how the pyridine containing ligand bound to a solid support compound of Formula 2 may be used to concentrate and remove desired ions. The pyridine ligand containing solid support compound is placed in a column. An aqueous source solution containing the desired metal ion or ions, in a mixture of other metal ions which may be in a much greater concentration, is passed through the column. The flow rate for the solution may be increased by applying pressure with a pump on the top of the column or applying a vacuum in the receiving vessel. After the source solution has passed through the column, a much smaller volume of a recovery solution i.e. an aqueous solution, which has a stronger affinity for the desired metal ions than does the pyridine containing ligand, is passed through the column. This receiving solution contains only the desired metal ions in a concentrate form for subsequent recovery. Suitable receiving solutions can be selected from the group consisting of $Na_2S_2O_3$, thiourea, HI, HCl, NaI, $Na_4EDTA$, $Na_3NTA$, $NH_3$, $NH_4OH$, ethylenediamine and mixtures thereof. The preceding listing is exemplary and other receiving solutions may also be utilized, the only limitation being their ability to function to remove the desired metal ions from the pyridine ligands.

The following examples of separations and recoveries of transition metal ions by the inorganic support-bound pyridine containing ligands which were made as described in Examples 4 through 6 are given as illustrations. These examples are illustrative only, and are not comprehensive of the many separations of metal ions that are possible using the materials of Formula 2.

EXAMPLE 7

In this example, 2 grams of the silica gel-bound dipyridylmonoamine (dipicolylamine) of Example 4 were placed in a column 1.9 cm in diameter and 2.3 cm long. A 250 ml solution of 0.001 M $CuCl_2$ in 1M HCl and 0.1M $FeCl_3$ was passed through the column using a vacuum pump at 100 torr to increase the flow rate. Atomic absorption spectroscopic analysis of the solution after passing through the column revealed that 98% of the $Cu^{2+}$ had been removed. Another 500 mls of 0.001M $CuCl_2$ in 1M HCl and 0.1M $FeCl_3$ was passed through the column to load the maximum amount of $Cu^{2+}$ that could possibly be loaded in this matrix. After washing the column with distilled water, a 10 ml aqueous recovery solution of 2M ethylenediamine and 1M HCl was passed through the column. An analysis of the recovery solution by atomic absorption spectroscopy showed that an amount of $Cu^{2+}$ equivalent to the moles of the bound ligand (0.2 mmoles/g) was collected and no $Fe^{3+}$ could be detected.

EXAMPLE 8

In this example, 2 grams of the silica gel-bound tripyridyldiamine of Example 5 were placed in a column as described in Example 7. A 250 ml solution of 40 ppm $Mn^{2+}$ present as the $Cl^-$ salt in 0.1M Na-acetate was passed through the column using a vacuum pump at 100 torr to increase the flow rate. After washing the column with distilled water, a 10 ml aqueous recovery solution of 3M HCl was passed through the column. Atomic absorption analysis of the original solution after passing through the column and the recovery solution indicated that the $Mn^{+2}$ was removed to a 1.6 ppm level and all of the $Mn^{+2}$ removed was recovered in the recovery solution within experimental error. Furthermore, the $Na^+$ in the recovery solution was below detection.

EXAMPLE 9

In this example, 2 grams of the silica gel-bound dipyridyltetraamine of Example 6 were placed in a column as described in Example 7. A 250 ml solution of 10 ppm $Pd^{2+}$, 10 ppm $Ir^{3+}$, and 10 ppm $Rh^{3+}$ in 0.1M HCl and 0.1M NaCl was passed through the column using a vacuum pump at 100 torr to increase the flow rate. Atomic absorption spectroscopic analysis of the solution after passing through the column revealed that the $Pd^{2+}$ level was below detection and the $Ir^{3+}$ and $Rh^{3+}$ levels were at 0.5 ppm each. After washing the column with water, a 10 ml aqueous recovery solution of 2M $NH_4OH$ and 1M HCl was passed through the column. An analysis of the recovery solution by atomic absorption spectroscopy showed that all of the $Pd^{2+}$, $Ir^{3+}$, and $Rh^{3+}$ in the column were recovered within experimental error.

From the foregoing, it will be appreciated that the inorganic solid support bound pyridine-containing hydrocarbon ligands of Formula 2 of the present invention provide a material useful for the separation and concentration of the transition metal cations from mixtures of those cations with other metal cations and $H^+$. The transition metals can then be recovered from the concentrated recovery solution by standard techniques known in the art. Similar examples have also been successfully established for many other transition metal ions.

Although the invention has been described and illustrated by reference to certain specific inorganic solid support-bound pyridine-containing hydrocarbon ligands of Formula 2 and processes of using them, analogs, as above defined, of these pyridine-containing hydrocarbon ligands are within the scope of the compounds and processes of the invention as defined in the following claims.

We claim:

1. A method for the concentration and removal of desired heavy metal ions from a source solution which comprises
  (a) bringing said source solution having a first volume into contact with a compound comprising a pyridine containing ligand covalently bonded to a solid inorganic support having the formula:

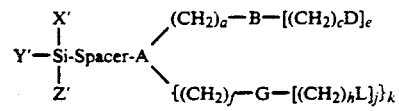

wherein Spacer is a 1 to 10 carbon member hydrophilic grouping; A is a member selected from the group consisting of N, NH, S and O; B, D, G, and L are each members selected from the group consisting of $NR_x$, 2-pyridyl or substituted 2-pyridyl, with x being 1 if NR is an intermediate part of a pyridine ligand and x being 2 if NR is at the terminal end of a pyridine ligand; a, c, g and h are each integers ranging from 1 to 5; e and j are each integers ranging from 0 to 5; and k is an integer of 0 or 1; with the proviso that k must be 0 when A is NH, S or O and k must be 1 when A is N; R is a member selected from the group consisting of H, lower alkyl, substituted lower alkyl, pyridyl or substituted pyridyl; with the further proviso that at least one of B or D and G or L must be 2-pyridyl or substituted 2-pyridyl and X', Y' and Z' are each a member selected from the group consisting of Cl, Br, I, alkyl, alkoxy, substituted alkyl, substituted alkoxy and O-solid support with the proviso that at least one of X', Y' and Z' must be O-solid support; said pyridine containing ligand portion of said compound having an affinity for the desired heavy metal ions to form a complex between said desired heavy metal ions and said pyridine containing ligand portion of said compound;

(b) removing said source solution from contact with said compound to which said desired heavy metal ions have been complexed; and (c) contacting said compound having said desired heavy metal ions complexed thereto with a smaller volume of a receiving solution having a greater affinity for said desired heavy metal ions than said compound thereby breaking said complex and recovering the desired heavy metal ions in concentrated form in said smaller volume of said receiving solution.

2. A method according to claim 1 wherein said pyridine containing ligand covalently bonded solid supported compound is contained in a packed column and wherein said source solution is first flowed through said column wherein said desired heavy metal ions are removed from said source solution by the formation of a complex between said desired heavy metal ions and said pyridine containing ligand portion of said compound followed by the breaking of said complex and removal of said desired heavy metal ions from said packed column by flowing said smaller volume of said receiving solution through said packed column and recovering said receiving solution containing said desired heavy metal ions in concentrated form.

3. A method according to claim 2 wherein the O-solid support is a member selected from the group consisting of silica, zirconia, titania, alumina, nickel oxide or any other similar hydrophilic inorganic support materials.

4. A method according to claim 3 wherein Spacer is a member selected from the group consisting of lower alkyl, aryl, glycidyl and alkylamino.

5. A method according to claim 4 wherein the desired heavy metal ions are embers selected from the group consisting of $Cu^{2+}$, $Ni^{2+}$, $Zn^{2+}$, $Mn^{2+}$, $Co^{2+}$, $Cd^{2+}$, $Hg^{2+}$, $Pd^{2+}$, $Rh^{3+}$, $Co^{3+}$, $Fe^{2+}$, $Ir^{3+}$, $Pt^{2+}$, $Pt^{4+}$ and $Ru^{3+}$.

6. A method according to claim 5 wherein the source solution additionally contains $H^+$ ions.

7. A method according to claim 5 wherein the source solution is a solution selected from a water supply source, a waste solution containing emulsions from treatment of photographic film or a waste solution from treatment of x-ray film.

8. A method according to claim 5 wherein Spacer is glycidyl and O-solid support is O-silica.

9. A method according to claim 8 wherein the pyridine containing ligand covalently bonded to a solid inorganic support has the formula:

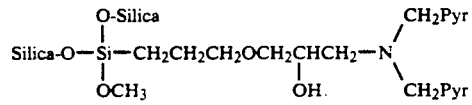

10. A method according to claim 8 wherein the pyridine containing ligand covalently bonded to a solid inorganic support has the formula:

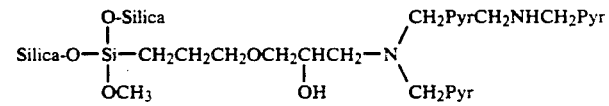

11. A method according to claim 8 wherein the pyridine containing ligand covalently bonded to a solid inorganic support has the formula:

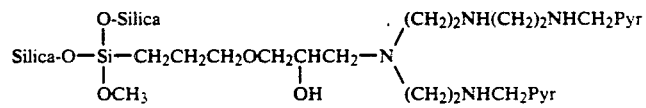

12. A method according to claim 3 wherein the

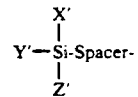

portion of the compound is a reaction product of O-solid hydrophilic support material with a silicon containing spacer grouping selected from the group consisting of dimethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl)phenyltrimethoxysilane; vinyltriethoxysilane; 3-bromopropyltriethoxysilane; 3-glycidoxypropyltrimethoxysilane; and combinations thereof.

13. A method according to claim 5 wherein the receiving solution is selected from the group consisting of $Na_2S_2O_3$, thiourea, HI, HCl, NaI, $Na_4EDTA$, $Na_3TNA$, $NH_3$, $NH_4OH$, ethylenediamine and mixtures thereof.

* * * * *